United States Patent [19]

Sakamoto et al.

[11] Patent Number: 5,292,952
[45] Date of Patent: Mar. 8, 1994

[54] PROCESS FOR PRODUCING 2-FLUORO-4-(TRIFLUOROMETHYL) ACETANILIDE

[75] Inventors: Noriyasu Sakamoto, Nishinomiya; Toshiaki Taki, Toyonaka; Noritada Matsuo, Itami, all of Japan

[73] Assignee: Sumitomo Chemical Company, Limited, Osaka, Japan

[21] Appl. No.: 978,888

[22] Filed: Nov. 19, 1992

[30] Foreign Application Priority Data

Nov. 20, 1991 [JP] Japan .................... 3-304609

[51] Int. Cl.$^5$ .................................. C07C 233/15
[52] U.S. Cl. ............................ 564/218; 564/215; 564/217
[58] Field of Search ............. 564/218, 217, 215; 514/625

[56] References Cited

U.S. PATENT DOCUMENTS 5,025,107  6/1991  Chamberlin .................. 564/414

OTHER PUBLICATIONS

Harland et al., Synthesis, Nov. 1984, 941-943.
Aldrich et al, J. Med. Chem., 1971, 14, 535-543.
Kagaku Yogo Jiten (Dictionary of Chemical Terms), Third Edition, May 16, 1992, p. 684.

*Primary Examiner*—Glennon H. Hollrah
*Assistant Examiner*—Shailendra Kumar
*Attorney, Agent, or Firm*—Cushman, Darby & Cushman

[57] ABSTRACT

Disclosed is a process for producing 2-fluoro-4-(trifluoromethyl) acetanilide which comprises reacting 3,4-difluorobenzotrifluoride with acetamide in the presence of a base in an aprotic polar solvent or in a mixture of an aprotic polar solvent and an aprotic non-polar solvent.

12 Claims, No Drawings

PROCESS FOR PRODUCING 2-FLUORO-4-(TRIFLUOROMETHYL) ACETANILIDE

FIELD OF THE INVENTION

This invention relates to an industrially advantageous process for producing 2-fluoro-4-(trifluoromethyl-)acetanilide, which is useful as an intermediate for the production of insecticides.

BACKGROUND OF THE INVENTION

The so-far known processes for producing 2-fluoro-4(trifluoromethyl)acetanilide as described in J. Org. Chem., 50, 4576 (1985) and EP-A-0246061 may be illustrated as follows:

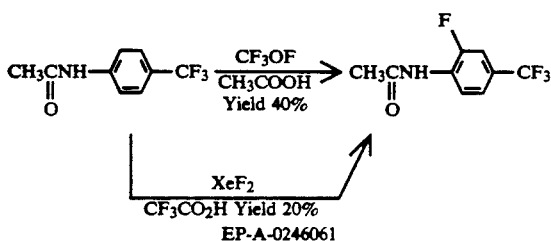

J. Org. Chem., 50, 4576 (1985)

However, these processes are not necessarily satisfactory for the commercial production of 2-fluoro-4(trifluoromethyl)acetanilide. That is to say, trifluoromethyl hypofluorite is hardly available because of the necessity of special fluorine-handling techniques, while xenon difluoride is an expensive reagent and the fluorination therewith is not very regioselective, hence the purity of the product is not good. Furthermore, these processes give only low yields and cannot be said to be advantageous from the commercial standpoint,

SUMMARY AND DESCRIPTION OF THE INVENTION

Under the circumstances, we made intensive investigations in an attempt to develop a process for producing 2-fluoro-4-(trifluoromethyl)acetanilide which is much improved from the industrial viewpoint. As a result, we found that the object can be achieved when the method mentioned below is used. Based on this finding, we have completed the present invention.

The invention thus provides a process for producing 2-fluoro-4-(trifluoromethyl)acetanilide which comprises reacting 3,4-difluorobenzotrifluoride with acetamide in the presence of a base in an aprotic polar solvent or in a mixture of an aprotic polar solvent and an aprotic non-polar solvent.

As for the amounts of the reactants, acetamide and the base are each used generally in an amount of about 1 to about 10 moles, preferably (from the viewpoint of the reaction yield and the economics) about 1.8 to about 2.2 moles, per mole of 3,4-difluorobenzotrifluoride. The reaction is carried out at a temperature within the range of usually about 30° to about 160° C., preferably about 40° to about 100° C., usually for a period of about 0.5 to about 100 hours.

The base includes a non-nucleophilic strong base, for example, an alkali metal hydride such as sodium hydride, or an alkali metal carbonate such as potassium carbonate.

The aprotic polar solvent includes, among others, dimethylformamide, dimethyl sulfoxide, hexamethylphosphoric triamide, sulfolane, N-methylpyrrolidone, 1,3-dimethyl-2-imidazolidinone, 1,3-dimethyl-3,4,5,6-tetrahydro-2-(1H)-pyrimidone, acetonitrile, tetrahydrofuran and dioxane, and mixtures of these.

Furthermore, as a solvent, a mixture of an aprotic polar solvent and an aprotic non-polar solvent may also be used. The aprotic non-polar solvent is preferably, for example, an aromatic hydrocarbon (e.g. $C_6$–$C_8$) such as benzene, toluene, etc., an aliphatic hydrocarbon (e.g. $C_6$–$C_8$) such as hexane, heptane etc., or a halogenated hydrocarbon (e.g. $C_1$–$C_6$) solvent such as chloroform, carbon tetrachloride, chlorobenzene, etc, and mixture of these. When such mixture of an aprotic polar solvent and an aprotic non-polar solvent is used as the reaction solvent, the amount of the aprotic polar solvent is preferably more than 50 wt.% based on the weight of said mixture.

In order to isolate the desired product, namely 2-fluoro-4-(trifluoromethyl) acetanilide, the reaction mixture is first treatd with water or a diluted acid, such as aqueous hydrochloric acid, aqueous ammonium chloride, aqueous citric acid and then subjected to organic solvent extraction and concentration. Examples of organic solvent useful for the extraction is diethyl ether, diisopropyl ether, dichloromethane, chloroform, carbon tetrachloride, benzene, toluene, xylene, chlorobenzene, bromobenzene, ethyl acetate, n-hexane or n-heptane. If necessary, the desired product 2-fluoro-4(trifluoromethyl)acetanilide can further be purified by recrystallization or chromatography, for instance.

If desired, unreacted 3,4-difluorobenzotrifluoride can be recovered from the reaction mixture by distillation or by organic solvent extraction followed by distillation. If the reaction mentioned above is carried out in a reactor equipped with a distillation apparatus, the unreacted 3,4-difluorobenzotrifluoride can directly be recovered by distillation of the reaction mixture. For conducting the organic solvent extraction, the reaction mixture is treated with water or a diluted acid such as aqueous hydrochloric acid, and then subjected to extraction using a low-boiling organic solvent such as diethyl ether, dichloromethane, n-hexane etc. After separation of the aqueous layer, the organic layer is distilled, whereby the unreacted 3,4-difluorobenzotrifluoride is recovered. As a result, the desired product, 2-fluoro-4-(trifluoromethyl) acetoanilide is also obtained as a residue.

The desired product 2-fluoro-4-(trifluoromethyl) acetanilide can be converted, upon hydrolysis (deacetylation), to 4-amino-3-fluorobenzotrifluoride, which in turn is converted to benzoylurea insecticides, as described, for instance, in EP-A-0246061. The conversion of 2-fluoro-4-(trifluoromethyl)acetanilide to 4-amino-3-fluorobenzotrifluoride by hydrolysis is also described in detail in Reference Example 1 to be set forth later.

The starting material for carrying out the process of the invention, namely 3,4-difluorobenzotrifluoride, can be prepared, for instance, by the method described in U.S. Pat. No. 4,937,396.

The following working examples and reference example are further illustrative of the present invention but are by no means limitative of the scope thereof.

EXAMPLE 1

A reactor was charged with 13.6 g (0.231 mole) of acetamide, 9.23 g of sodium hydride (60% w/w dispersion in mineral oil, 0.23 mole) and 200 ml of dimethylformamide, and the mixture was heated to 60° C. with stirring At that temperature, a solution of 20 g (0.11 mole) of 3,4-difluorobenzotrifluoride in 20 ml of dimethylformamide was added dropwise gradually to the reactor contents After completion of the dropwise addition, the reactor contents were heated to 100° C. and further stirred for an hour.

The reaction mixture was cooled to room temperature (about 20° C.) and then poured slowly into 5% hydrochloric acid, and the resultant mixture was extracted with two 300-ml portions of ethyl acetate. The ethyl acetate layers were combined, washed with water, dried over anhydrous sodium sulfate and concentrated to give a crude product. This crude product was subjected to silica gel column chromatography (eluent: n-hexane/ethyl acetate = 1/1) to give 18.7 g of 2-fluoro-4-(trifluoromethyl) acetanilide.

Yield 77%. Melting point 135.6° C.

EXAMPLE b 2

A reactor was charged with 0.32 g (5.42 mmoles) of acetamide, 0.22 g of sodium hydride (60% w/w disperision in mineral oil, 5.5 mmoles), 0.5 g (2.75 mmoles) of 3,4difluorobenzotrifluoride and 10 ml of dimethyl sulfoxide, and the mixture was heated to 60° C. with gentle stirring. Then, after stirring at 60-65° C. for 30 minutes, the reaction mixture was cooled to room temperature (about 20° C.) and slowly poured into 5% hydrochloric acid. The resultant mixture was extracted with two 200-ml portions of ethyl acetate. The ethyl acetate layers were combined, washed with water, dried over anhydrous magnesium sulfate and concentrated to give a crude product. This crude product was subjected to silica gel column chromatography (eluent: n-hexane/ethyl acetate = 1/1) to give 0.45 g of 2-fluoro-4-(trifluoromethyl) acetanilide.

Yield 95%. Melting point 135.4° C.

REFERENCE EXAMPLE 1

A reactor was charged with 10.0 g of 2-fluoro-4(trifluoromethyl)acetanilide, 50 ml of 20% aqueous sulfuric acid and 50 ml of methyl alcohol, and the mixture was stirred under reflux for 4 hours. The reaction mixture was cooled to room temperature (about 20° C.) and then made weakly alkaline by slowly adding a 5% aqueous solution of sodium hydrogen carbonate. The resultant solution was then extracted with two 200-ml portions of diethyl ether. The diethyl ether layers were combined, washed with water, dried over anhydrous magnesium sulfate and concentrated to give a crude product. This crude product was subjected to silica gel column chromatolography (eluent: n-hexane/ethyl acetate = 4/1 ) to give 7.29 g of 4-amino-3-fluorobenzotrifluoride.

Yield 90%. Refractive index $n_D^{22.5} = 1.4642$.

As a process for producing 2-fluoro-4-(trifluoromethyl)acetanilide, the process of the invention is advantageous over the prior art methods from the industrial standpoint since the desired product can be obtained with high selectivity and high yield by reacting 3,4-difluorobenzotrifluoride with acetamide which is inexpensive.

We claim:

1. A process for producing 2-fluoro-4-(trifluoromethyl) acetanilide which comprises reacting 3,4-di-fluorobenzotrifluoride with acetamide in the presence of alkali metal hydride or alkali metal carbonate in a solvent selected from the group consisting of at least one aprotic polar solvent and a mixture of at least one aprotic solvent and at least one aprotic non-polar solvent.

2. A process as claimed in claim 1, wherein said base is an alkali metal hydride.

3. A process as claimed in claim 1, wherein said base is sodium hydride.

4. A process as claimed in claim 1, wherein the aprotic polar solvent is at least one member selected from the group consisting of dimethylformamide, dimethyl sulfoxide, hexamethylphosphoric triamide, sulfolane, N-methylpyrrolidone, 1,3-dimethyl-2-imidazolidinone, 1,3-dimethyl-3,4,5,6-tetrahydro-2-(1H)-pyrimidone, acetonitrile, tetrahydrofuran and dioxane.

5. A process as claimed in claim 1, wherein the aprotic polar solvent is dimethylformamide or dimethyl sulfoxide.

6. A process as claimed in claim 1, wherein the aprotic polar solvent is dimethyl sulfoxide.

7. A process as claimed in claim 1, wherein acetamide and the base are used each in an amount of about 1 to about 10 moles per mole of 3,4-difluorobenzotrifluoride.

8. A process as claimed in claim 1, wherein the reaction is carried out at a temperature within the range of about 40° to about 100° C.

9. A process for producing 2-fluoro-4-(trifluoromethyl) acetanilide which comprises reacting 3,4-di-fluorobenzotrifluoride with acetamide in the presence of a non-nucleophilic base selected from the group consisting of alkali metal hydride and alkali metal carbonate in (i) at least one aprotic polar solvent selected from the group consisting of dimethylformamide, dimethyl sulfoxide, hexamethylphosphoric triamide, sulfolane, N-methylpyrrolidone, 1,3-dimethyl-2-imidazolidinone, 1,3-dimethyl-3,4,5,6-tetrahydro-2-(1H)-primidone, acetonitrile, tetrahydrofuran and dioxane, or (ii) a mixture of at least one of said aprotic polar solvents and aprotic non-polar solvent selected from the group consisting of $C_6$–$C_8$ aromatic hydrocarbons, $C_6$–$C_8$ aliphatic hydrocarbons, $C_1$–$C_6$ halogenated hydrocarbons, and mixtures thereof.

10. A process as claimed in claim 9 wherein acetamide and base are used each in an amount of about 1 to about 10 moles per mole of 3,4-difluorobenzotrifluoride.

11. A process as claimed in claim 9 wherein the reaction is carried out at a temperature within the range of about 40° C. to about 100° C.

12. A process as claimed in claim 9 wherein a non-polar aprotic solvent is present, and is selected from the group consisting of benzene, toluene, hexane, heptane, chloroform, carbon tetrachloride, chlorobenzene, and mixtures thereof.

* * * * *